United States Patent [19]

Miura et al.

[11] Patent Number: 5,407,568
[45] Date of Patent: Apr. 18, 1995

[54] SEPARATION COLUMN CONTAINING S-CARBOXYALKYLCYSTEINE

[75] Inventors: Junkichi Miura, Hitachi; Kenji Yasuda, Tokyo; Mitsuo Ito, Ibaraki; Masahito Ito, Katsuta, all of Japan

[73] Assignee: Hitachi, Ltd., Tokyo, Japan

[21] Appl. No.: 118,704

[22] Filed: Sep. 9, 1993

[30] Foreign Application Priority Data

Sep. 17, 1992 [JP] Japan .................. 4-247557

[51] Int. Cl.⁶ .............................................. B01D 15/08
[52] U.S. Cl. .................. 210/198.2; 210/635; 210/656; 96/101
[58] Field of Search ......... 210/635, 656, 198.2; 436/66, 67, 161; 530/385, 413, 416, 417; 96/101

[56] References Cited

U.S. PATENT DOCUMENTS

| | | | |
|---|---|---|---|
| 4,407,961 | 10/1983 | Sanders | 436/67 |
| 4,810,391 | 3/1989 | Bruegger | 210/198.2 |
| 4,879,039 | 11/1989 | Takahashi | 210/656 |
| 5,358,639 | 10/1994 | Yasuda | 210/635 |

FOREIGN PATENT DOCUMENTS

| | | | |
|---|---|---|---|
| 0368092 | 5/1990 | European Pat. Off. | 210/198.2 |
| 0563865 | 10/1993 | European Pat. Off. | 210/198.2 |
| 3908302 | 9/1989 | France | |
| 63-75558 | 4/1988 | Japan | 210/198.2 |
| 2196810 | 8/1990 | Japan | 210/198.2 |
| 3255360 | 11/1991 | Japan | 210/198.2 |
| 1081740 | 8/1967 | United Kingdom | |

OTHER PUBLICATIONS

PTO Translation of Japan Patent 63-75558 by Y. O. on Mar. 16, 1994 pp. 1–4.
WPI, Week 8411, Derwent Publications Ltd., London, GB, AN 84-066388 & JP-A-59-023 247, Jun. 2, 1984, (Japan Elect Optics Lab).
Chuichi Hirayama and Yoshio Okamoto: Resin for Chromatography, published by Kyoritsu Shuppan K.K. (1989), pp. 1–3.

*Primary Examiner*—Ernest G. Therkorn
*Attorney, Agent, or Firm*—Kenyon & Kenyon

[57] ABSTRACT

Deterioration of performance of a separation column for liquid chromatograph due to changes in the functional groups during the preservation or application is prevented by filling a solution containing a component in the molecule with the same structure as that of the chemical function group of a packing material for the separation column as a filling liquid together with the packing material in the separation column, and also by washing the separation column with the same filling liquid as a washing solution after the analysis and retaining the washing solution therein, whereby the preservation stability of the separation column is improved and the separation column can be preserved at room temperature.

6 Claims, 4 Drawing Sheets

SEPARATION COLUMN CONTAINING S-CARBOXYALKYLCYSTEINE

BACKGROUND OF THE INVENTION

1. Field of the Invention

The present invention relates to a separation column for use in liquid chromatography, particularly a separation column with an improved preservation stability, and a method for preventing deterioration of a separation column, a method for transporting a separation column and a method for treating a separation column, directed to improvement of the preservation stability, and a filling liquid for a separation column, suitable for enhancing the preservation stability.

2. Related Prior Art

Separation columns and packing materials for use in liquid chromatography are disclosed in detail in Chuichi Hirayama and Yoshio Okamoto: Resin for Chromatography, published by Kyoritsu Shuppan K.K. (1989), where new materials directed particularly to higher functioning of packing materials and possible extension of application fields of packing materials are mentioned.

Separation columns using the new materials directed to higher functioning as a packing material have such problems as a relatively poor stability, faster deterioration during the preservation period from the preparation of the columns to their application or even after their application, that is, shorter life, than ordinary separation columns.

Recently, liquid chromatograph directly solely to clinical chemical analysis has been commercially available. When an operator carries out liquid chromatography with a considerably deteriorated separation column without paying any attention to the deteriorated state, identification errors are liable to occur, or improper calibration of the base line is liable to occur, resulting in involvement of larger errors in quantitative determination. When the operator, paying an attention to deterioration of the separation column, changes parameters of the liquid chromatograph or exchanges the deteriorated separation column with a fresh one, the identification errors can be prevented, but the operator is forced to do such an additional complicated work.

Furthermore, it is difficult to prepare quite identical separation columns, even if the same packing material is packed in the columns, and thus in case of separation columns of shorter life the exchange frequency of columns is increased, resulting in an increase in the risk of deterioration of the resulting chromatogram quality. Thus, some of the separation columns must be preserved in a chilled state to prevent the deterioration during the preservation. However, this procedure has required much time and an additional control means for the preservation and transportation of the separation column.

SUMMARY OF THE INVENTION

An object of the present invention is to provide a separation column capable of preventing deterioration of performance of a packing material through a simple structure without any special chilled preservation means during the preservation period from the time of preparation to the time of application or even after the application.

Another object of the present invention is to provide a method for transporting a separation column, which can prevent deterioration of properties of a packing material during the transportion of the separation column.

Other object of the present invention is to provide a method for treating a separation column, which can prevent deterioration of properties of a packing material in the treatment of the separation column in sample analysis.

Further object of the present invention is to provide a filling liquid for a separation column, the filling liquid being to be filled in the separation column together with a packing material, and being capable of preventing deterioration of properties of the separation column.

As a result of studies on a method for preventing changes in the separation performance, retention time, etc. during the preservation or after the application in order to solve these problems, the present inventors have found that the deterioration of the properties of the separation column is due to changes in chemical functional groups introduced into the packing material, and have established the present invention on the basis of this finding. That is, according to the present invention these problems can be solved by using a solution containing molecules with the same structure as that of the packing material as a filling liquid for the separation column, thereby preventing the packing material in a separation column from changes during the preservation, and keeping the separation column in a less deteriorated state as to the column performance for a long time during the preservation period or even after the application.

According to the present invention, the separation column is transported after the solution containing molecules with the same structure as that of the packing material is filled in the separation column together with the packing material.

Furthermore, according to the present invention, the separation column is treated in sample analysis by passing the solution containing molecules with the same structure as that of the packing material through the separation column after a sample solution has been passed through the separation column.

Still furthermore, according to the present invention the solution containing molecules with the same structure as that of the packing material is used as a filling liquid in order to prevent deterioration of performance of the separation column.

DETAILED DESCRIPTION OF THE INVENTION

Functions of the present invention will be explained in detail below.

Supports to which functional groups are to be introduced in the present invention include, for example, silica gel, organic polymer gels, etc. Explanation will be made, referring to methacrylate-based gel typical of the organic polymer gels.

Monomers for use in gel synthesis include, for example, hydrophilic methacrylates, etc. such as hydroxyethyl methacrylate, polyethyleneglycol methacrylate, glycerol methacrylate, etc.

Cross-linking agents for use in the gel synthesis include, for example, polyfunctional methacrylate esters, etc. such as ethyleneglycol dimethacrylate, diethyleneglycol dimethacrylate, triethyleneglycol dimethacrylate, etc. Polymerization of the monomer and the cross-linking agent is not particularly limited, and ordinary processes can be utilized for the polymerization. Polymerization and introduction of ion exchange groups can be carried out by processes disclosed in JP-A 2-196810 and JP-A 3-2553601.

The gel prepared by any of these processes is packed in a column of stainless steel or synthetic resin to prepare a separation column. Packing procedure is not particularly limited. For example, packing can be carried out by a slurry packing procedure comprising suspending a gel in an aqueous dilute solution of a salt, thereby preparing a slurry of the gel, and packing the slurry into a separation column under high pressure.

In case of a separation column filled with a gel into which carboxyl groups or carboxyalkyl groups have been introduced as weak cation exchange groups, deterioration of performance, particularly a decrease in the retention time, due to drop-out of ion exchange groups, dehydration condensation of ion exchange groups themselves, etc. is observable during the preservation even in a non-used state even after the packing.

Even in such a separation column, the above-mentioned changes of ion exchange groups can be suppressed by using an aqueous solution containing carboxyl groups or carboxyalkyl groups as a filling liquid for the separation column, and as a result deterioration of the performance, such as a decrease in the retention time, etc. can be prevented.

PREFERRED EMBODIMENTS OF THE INVENTION

Figure 1A:
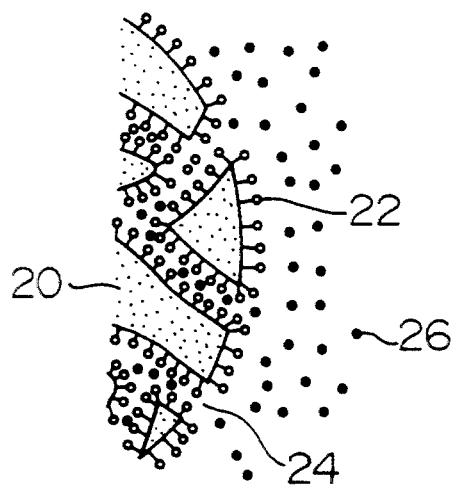
FIGS. 1A and 1B are diagrams each showing the states of packing materials in a comparative example and an embodiment of the present invention, respectively.

Embodiments of the present invention will be explained below, referring to the drawings.

Analysis of hemoglobins in human blood was carried out in analysis using a liquid chromatograph. In the embodiments of the present invention, explanation will be made mainly of a separation column packed with a packing material directed to analysis of hemoglobins, but the packing material to which the present invention is applicable is not limited to that directed to that sole purpose.

It is practical to use S-carboxymethylcysteine among S-carboxyalkylcysteines as a component of the filling liquid for preventing deterioration of the packing materials, but S-carboxyethylcysteine can be also used for the purpose of attaining the same function. In Examples which follow, explanation will be made, referring to S-carboxymethylcysteine typical of S-carboxyalkylcysteine.

EXAMPLE 1

A cation exchange gel was prepared by introducing carboxymethyl groups according to the procedure disclosed in JP-A 2-196810. The gel was washed with warm water and then subjected to quantitative determination of carboxymethyl groups. It was found that 0.33 m eq./g of carboxyl groups were introduced therein. Then, the ion exchanger was packed into a column, 4.6 mm in diameter and 35 mm long, to prepare a separation column for analysis of glycated hemoglobins.

Figure 2:
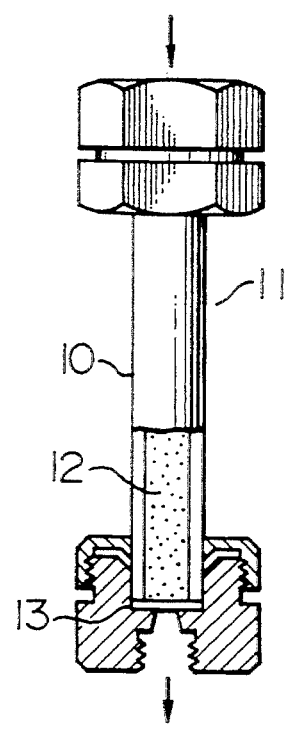
FIG. 2 is a structural view of a separation column according to one embodiment of the present invention.

The thus prepared separation column is shown in FIG. 2, where a separation column 10 packed with an ion exchanger 12 is encased in a chromatographic column 11, and a porous filter 13 is provided in a passage through which a sample solution is passed.

One of two separation columns 10 was filled with a filling liquid containing molecules with the same structure as that of a packing material and another separation column 10 was filled only with a filling liquid containing no such molecules.

It was preferable that filling liquid for preventing deterioration of the separation columns had a neutral pH, particularly a pH ranging from 5 to 9, and thus aqueous solutions containing 0.1 mol/l of sodium chloride were used as a base for the filling liquid. A concentration of molecules with the same structure as that of the packing material and to be dissolved into the filling liquid was 0.1 to 100 m mol/l, preferably 1 to 10 m mol/l, and thus 2 m mol/l of S-carboxymethylcysteine was added to the base filling liquid.

Figure 1B:
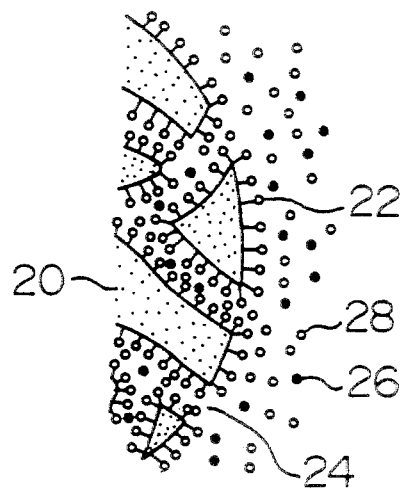

FIGS. 1A and 1B are schematic views showing the states of particles of the packing material and the filling liquid filled in the separation columns, respectively. The packing material was sealed into a chromatographic column, and had about 50% of interstitial fraction within the column on the basis of total column volume, when packed under the normal pressure. The filling liquid existed around the particles of the packing materials. Synthetic resin supports 20 had ion exchange functional groups 22 and the filling liquid existed around the supports 20 and within pores 24. FIG. 1A shows the case that the filling liquid was an aqueous solution of only sodium chloride 26, whereas FIG. 1B shows the state of the separation column according to the present invention, where S-carboxymethylcysteine 28 existed in the filling liquid together with sodium chloride 26. These separation columns were mounted on analyzers, respectively.

Analyzers were provided each with a feed pump Type L-6300 and a detector Type L-4200 (both types made by Hitachi, Ltd., Japan). Stepwise elution was carried out with three kinds of eluents (eluent A, eluent B and eluent C) having different salt concentrations with a detection wavelength of 415 nm.

The eluent A was a phosphate buffer solution at a concentration of 52.5 m mol/l (pH 6.2), the eluent B a phosphate buffer solution at a concentration of 67.5 m mol/l (pH 6.2) and the eluent C a phosphate buffer solution at a concentration of 210.0 m mol/l (pH 6.1) with the following eluent feeding time schedule: the eluent A: 0–0.2 min., the eluent B: 0.3–1.4 min., the eluent C: 1.5–1.8 min. and the eluent A: 1.9–3.5 min. at a flow rate of 1.2 ml/min and at a column temperature of 40° C. Assaying samples were bloods of normal subjects each diluted to 100-fold with 0.1% Triton X-100, a surfactant made by Rohm and Haas, USA.

Figure 3:
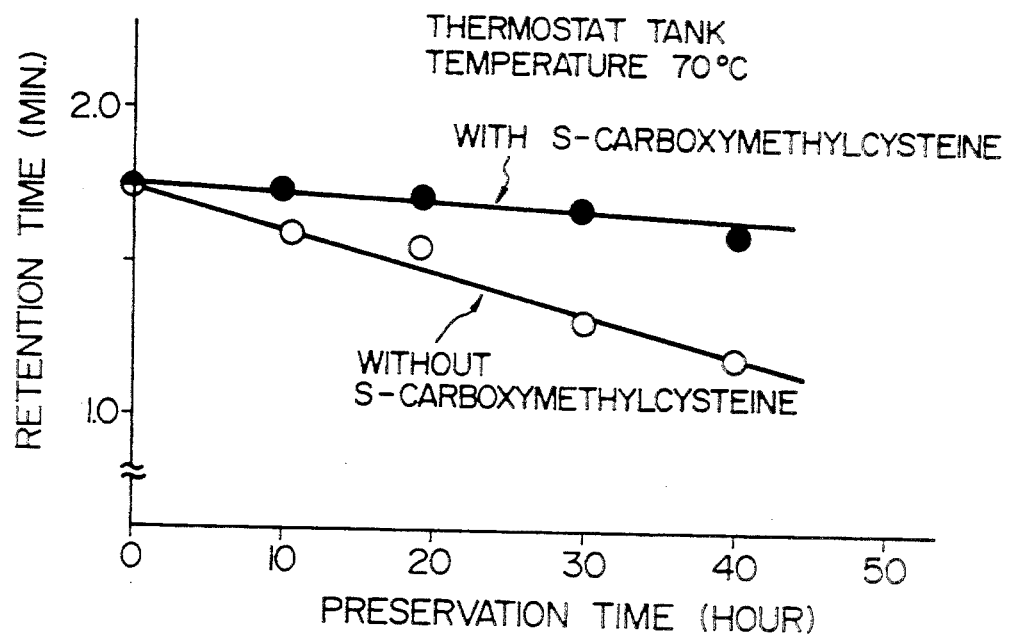
FIG. 3 is a diagram showing glycated hemoglobin $A_{1c}$ retention time between the separation column of Example 1 and the separation column of a comparative example, when hemoglobins were analyzed.

The separation column filled with the filling liquid containing S-carboxymethylcysteine and the separation column filled with the filling liquid containing no S-carboxymethylcysteine were preserved in a thermostat tank at 70° C. to investigate the stability during the preservation. The columns were mounted on the glycated hemoglobin analyzers, respectively, to investigate relations between the preservation time and the retention time of glycated hemoglobin $A_{1c}$. The results are shown in FIG. 3. As is apparent from FIG. 3, progress of deterioration of the separation column filled with the filling liquid containing S-carboxymethylcysteine was slower in the heat-accelerated deterioration test at 70° C. than that of the separation column filled with the filling liquid without S-carboxymethylcysteine and thus the former column had a better preservation stability.

Figure 4C:
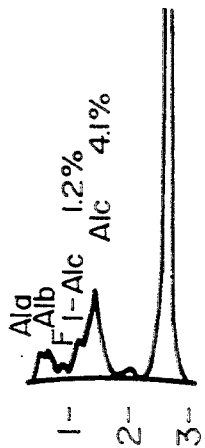
FIGS. 4A, 4B and 4C are chromatograms of a separation column of one embodiment of the present invention and that of a comparative example in comparative analyses in Example 1.
Figure 4B:
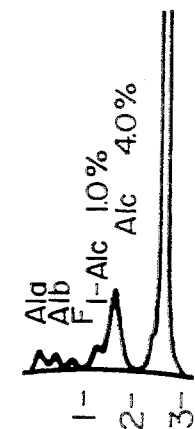
Figure 4A:
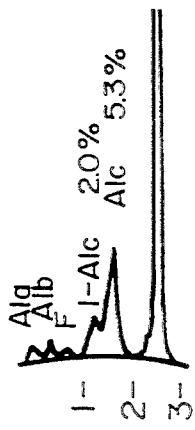

FIG. 4A shows a chromatogram of a separation column filled with a filling liquid containing S-carboxymethylcysteine and a separation column filled with the filling liquid without S-carboxymethylcysteine at the start of the test and FIG. 4B and FIG. 4C show chromatograms of the former column and the latter column 40 hours thereafter. The filling liquid containing S-carboxymethylcysteine precisely identified the respective components even 40 hours after the start of the test, as shown in FIG. 4B, whereas the filling liquid containing no S-carboxylmethylcysteine had considerably shorter retention time of peaks for components of earlier elution than $A_{1c}$, as shown in FIG. 4C, resulting in poor separation of $A_{1a}$ peak and $A_{1b}$ peak.

If the deterioration of the separation columns can be presumed to proceed according to the law of chemical reaction on the basis of these results, retention time for glycated hemoglobin $A_{1c}$ will be shorter by at least 0.2 minutes by deterioration of the column at about 13th day in case of the separation column filled with the filling liquid containing no S-carboxylmethylcysteine when preserved at room temperature (30° C.), and deterioration of the separation column will become obvious. On the other hand, when the separation column filled with the filling liquid containing S-carboxymethylcysteine according to the present invention is preserved likewise at 30° C., there will be a longer retention time, such as about 2 months, until deterioration of the separation column becomes obvious.

EXAMPLE 2

Figure 5:
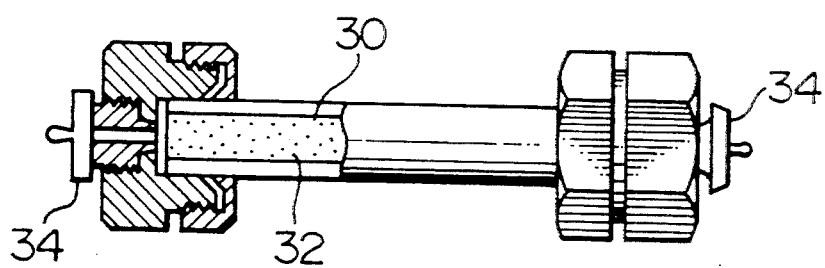
FIG. 5 is a structural view a transportable separation column according to one embodiment of the present invention.

FIG. 5 shows one embodiment of the present separation column in a transportable form. The transportable separation column is filled with a filling liquid 30 containing S-carboxylmethylcysteine together with a packing material 32 and is sealed with sealing plugs 34 at both ends so that the packing material may not be dried during the transportation.

Since the column is filled with a solution containing molecules with the same structure as that of the packing material for the column, deterioration of the separation column can be prevented only by preserving the column in a cool and dark place without any chilling according to the present method for transporting the separation column, whereas it is the conventional practice to preserve separation columns in a chilled place to suppress deterioration of the columns, for example, during the transportation from the preparation site of separation columns to the users' site of the separation columns and also until the users use the columns in analysis.

EXAMPLE 3

Figure 6:
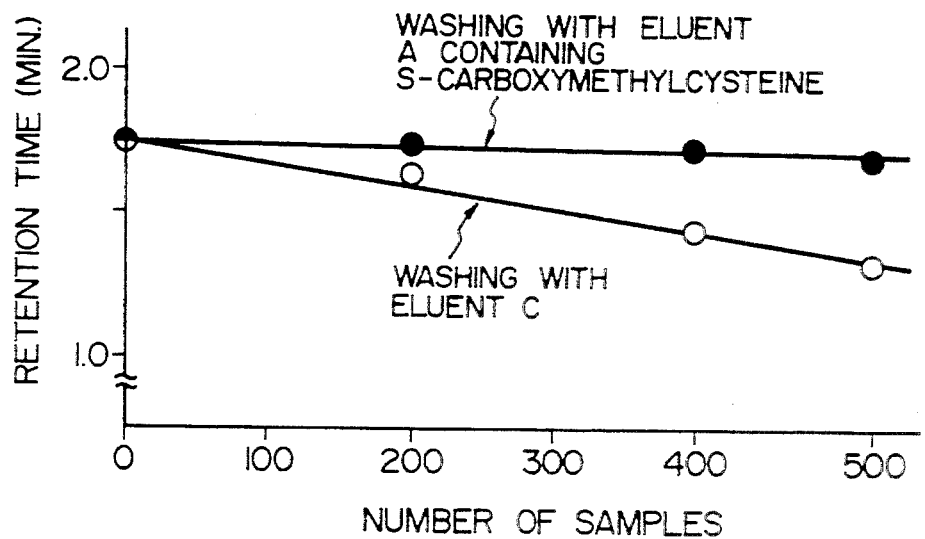
FIG. 6 is a diagram of glycated hemoglobin retention time between the separation column of Example 2 and a comparative example.

50 samples of hemoglobins were analyzed as a set in the analyzer of Example 1, using the separation columns and the eluents of Example 1, and the separation columns were left standing for 2 days after the end of analysis. Before being left standing, one of the columns was washed with the eluent A, a buffer phosphate solution at a concentration of 52.5 m mol/l (pH 6.2), further containing 2 m mol/l of S-carboxymethylcysteine for 20 minutes after the end of analysis, while other column was washed likewise with the eluent C, a buffer phosphate solution at a concentration of 210.0 m mol/l (pH 6.1) without S-carboxymethylcysteine for 20 minutes after the end of analysis. Changes in the retention time of hemoglobin $A_{1c}$ when the foregoing procedure was repeated are shown in FIG. 6. It can be seen from FIG. 6 that deterioration of the column washed with the solution containing S-carboxymethylcysteine after the end of each set of analysis and before being left standing proceeded more slowly and a higher stability could be obtained.

EXAMPLE 4

Figure 7:
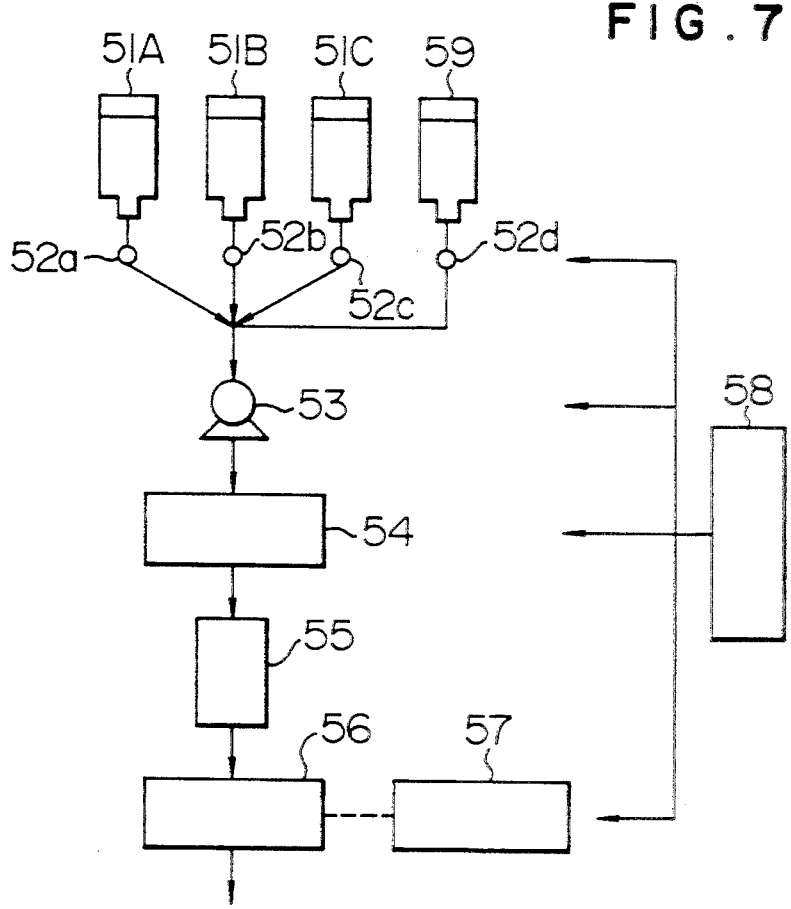
FIG. 7 is a flow diagram showing an analyzer for a single purpose according to one embodiment of the present invention.

Embodiment of an analyzer for a sole purpose according to the present invention is shown in FIG. 7.

In the analyzer directed solely to glycated hemoglobin analysis, a washing solution 59 not directly relating to the analysis and a switch valve 52d in the line so as to pass the washing solution 59 therethrough after the end of a set of analyses are provided. Eluents 51A to 51C are phosphate buffer solutions corresponding to eluents A, B and C of Example 1, respectively, and are fed to a separation column 55 through an autosampler 54 by a pump 53. Fractions containing hemoglobins are detected by a visible detector 56 and signals from the detector 56 are recorded in a data processor 57. Line switch valves 52a to 52c undergo repetitions of opening and closing at predetermined time intervals to obtain most appropriate chromatograms. The line switch valves 52a to 52d, the pump 53, the autosampler 54, the detector 56, and the data processor 57 are individually controlled by a computer 58. In this embodiment, the washing solution 59 containing S-carboxymethylcysteine is provided separately from the eluents.

As the washing solution, the same solution as the eluent can be used after dissolution of S-carboxymethylcycsteine therein. In this embodiment, an aqueous solution prepared by adding 2 m mol/l of S-carboxymethylcysteine to the eluent 51A is used. As a filling liquid for the separation column, an aqueous solution containing 0.1 mol/l of sodium chloride and 2 m mol/l of S-carboxymethylcysteine, as shown in Example 1, is filled in the separation column, thereby making the column ready for the analysis.

For only column stabilization purpose, a stabilizer can be added to all or some of the eluents 51A to 51C. However, since the stabilizer has the same structure as the functional groups of the packing material in the molecule, the stabilizer undergoes interaction with the interests in the sample. Thus, quite different separation from that when analyzed with eluents containing no stabilizer may take place, depending upon the kind and concentration of the stabilizer. In this embodiment, the washing solution 59 does not directly relate to the analysis, and thus the composition of the washing solution 59 can be selected without taking the data of separation into consideration.

Changes in the retention time of glycacted hemoglobin $A_{1c}$ investigated for analysis with the analyzer of this embodiment and for analysis with the analyzer of Example 1 without any washing with the washing solution containing S-carboxymethylcysteine have similar results to those shown in FIG. 6.

After passing the washing solution 59 through the separation column 55 by the pump 53 for a predetermined time, it is possible to retain the washing solution 59 within the separation column 55 by stopping the pump 53. Thus, it is possible to retard the deterioration of the separation column 55 during the period from the end of a set of analyses to the start of the successive set of analyses, thereby improving the stability.

Furthermore, since washing of the column can be carried out after the end of a set of analyses in the analyzer of this embodiment, composition of the washing solution can be selected without taking the separation pattern of hemoglobins into consideration, and the separation column can be effectively given a longer life without any special attention of an operator thereto.

As is apparent from the foregoing explanations, the stability of a separation column during the preservation can be increased by using a solution containing a component with the same structure in the molecule as that of the functional group introduced into a packing material as a filling liquid for the separation column, thereby enabling the column to be preserved and transported at room temperature and reducing the control steps. Furthermore, the stability can be increased by using a solution containing the same component as that of the filling liquid as a washing solution, thereby giving the separation column a longer life. The longer life can reduce the exchange frequency of the column, and thus can effectively prevent changes in the quality of analytical data due to the column exchange.

What is claimed is:

1. A separation column, which comprises a packing material having carboxyl groups or carboxyalkyl groups as ion exchange groups and a solution containing S-carboxyalkylcysteine, both filled in the separation column.

2. A separation column according to claim 1, wherein the S-carboxyalkylcysteine is S-carboxymethylcysteine.

3. A separation column according to claim 1, wherein the S-carboxyalkylcysteine is S-carboxyethylcysteine.

4. A separation column according to claim 1, wherein the solution containing the S-carboxyalkylcysteine has a neutral pH.

5. A separation column according to claim 1, wherein the solution contains the S-carboxyalkylcysteine at a concentration of 0.1 to 100 m mol/l.

6. A separation column, which comprises a cation exchange resin modified with carboxyl groups or carboxyalkyl groups and a solution containing S-carboxyalkylcysteine, both filled into the separation column.

* * * * *

UNITED STATES PATENT AND TRADEMARK OFFICE
CERTIFICATE OF CORRECTION

PATENT NO. : 5,407,568
DATED : 18 April 1995
INVENTOR(S) : Junkichi MIURA et al.

It is certified that error appears in the above-indentified patent and that said Letters Patent is hereby corrected as shown below:

| Column | Line | |
|--------|------|---|
| 1 | 31 | Change "chromatograph directly" to --chromatography directed--. |
| 1 | 39 | After "paying" delete "an". |
| 1 | 44 | Delete "such an". |
| 2 | 3 | Change "Other" to --Another--. |
| 2 | 8 | Change "Further" to --A further--. |
| 2 | 10 | After "being" delete "to be". |
| 3 | 43 | After "view" insert --of--. |
| 5 | 57 | Change "may not be dried" to --will not dry out--. |

Signed and Sealed this

Twenty-eighth Day of November 1995

Attest:

BRUCE LEHMAN

Attesting Officer    Commissioner of Patents and Trademarks